United States Patent [19]
Paglione

[11] 4,204,549
[45] May 27, 1980

[54] COAXIAL APPLICATOR FOR MICROWAVE HYPERTHERMIA

[75] Inventor: Robert W. Paglione, Robbinsville, N.J.

[73] Assignee: RCA Corporation, New York, N.Y.

[21] Appl. No.: 859,856

[22] Filed: Dec. 12, 1977

[51] Int. Cl.² ............................ G01K 7/02; A61N 5/02
[52] U.S. Cl. .................................... 128/784; 128/804; 73/359 R; 343/720; 333/245
[58] Field of Search ............... 128/2 A, 404, 399, 416, 128/736, 783, 804; 73/355 EM, 359 R; 219/10.55 A; 343/703, 718, 720; 324/58.5 R; 333/245

[56] References Cited

U.S. PATENT DOCUMENTS

| | | | |
|---|---|---|---|
| 1,156,317 | 10/1915 | Santos et al. | 128/413 |
| 1,923,916 | 8/1933 | Darbord | 343/703 |
| 2,126,257 | 8/1938 | Hird | 128/412 |
| 3,354,717 | 11/1967 | Minnicle | 73/204 |
| 3,684,172 | 8/1972 | Evalds | 73/359 |
| 3,794,914 | 2/1974 | Aslan | 343/703 |
| 3,796,977 | 3/1974 | Elliott et al. | 333/245 |
| 3,798,967 | 3/1974 | Gieles et al. | 128/692 |
| 3,963,892 | 6/1976 | Camph et al. | 219/10.55 M |

FOREIGN PATENT DOCUMENTS 2462165  4/1976  Fed. Rep. of Germany .... 219/10.55 B

OTHER PUBLICATIONS

Lenox, R. H. et al., *A Microwave Applicator for CNS Enzyme Deactivation*, in IEEE Trans on M-wave Theo. & Tech., vol. MTT-24, No. 1, pp. 58–61, Jan. 1976.

Lehman, J. F. et al., *Evaluation of a Microwave Contact Applicator*, in Arch. of Phys. Med & Rehabilitation, Mar. 1970, p. 143–146.

Larsen, L. et al., *A M-wave Decoupled Brain Temp. Trnsducer*, IEEE Trans on M-wave The. & Tech., vol. MTT-22, No. 4, pp. 438–444, Apr. 1974.

Doss, J. D. et al., "*A Tech. for Localized Heating in Tissue: An Adjunct to Tomor Therapy,*" in Med. Instrmntatn, vol. 10, No. 1, Jan-Feb. 1976, pp. 16–21.

*Primary Examiner*—Robert W. Michell
*Assistant Examiner*—Francis J. Jaworski
*Attorney, Agent, or Firm*—Samuel Cohen; Joseph D. Lazar; Robert L. Troike

[57] ABSTRACT

Apparatus for hyperthermia treatment provides transmission of microwave energy for irradiation of tissues and simultaneous and concurrent and continuous measurement of the temperature of the heated tissues at the site of the treatment. The microwave energy is supplied to the site of treated tissue by a coaxial applicator which is positioned near the tissue.

9 Claims, 7 Drawing Figures

COAXIAL APPLICATOR FOR MICROWAVE HYPERTHERMIA

CROSS REFERENCE TO RELATED APPLICATION

Of interest is the following pending U.S. Pat. application: Ser. No. 840,036 filed Oct. 6, 1977 by R. W. Paglione, entitled, "A Temperature Controller For a Microwave Heating System."

BACKGROUND OF THE INVENTION

1. Field of the Invention

This invention relates to hyperthermia treatment of living tissues and more particularly to radiation of microwave energy and simultaneous measurement of the temperature at the site of treatment.

2. Description of the Prior Art

Medical practitioners have known that a patient with a cancerous tumor can be successfully treated, by a process which raises the temperature of the tumor. This treatment is generally referred to as hyperthermia. One method of hyperthermia treatment utilizes microwave radiation energy. The temperature of the tissue irradiated by the microwave energy is a function of the power or intensity of the microwave signal applied to the body tissue. The depth of penetration of a microwave signal into the tissue is, in general, an inverse function of the signal frequency employed. The volume of the tissue to be treated is controlled by the electrical and geometrical design of the microwave applicator.

The microwave radiation may be controlled to elevate the temperature of a known volume of tissue. During microwave radiation, it is desirable to prevent overheating of the tissue as well as the surrounding tissues. It is correspondingly desirable to provide an accurate measurement of the temperature of the tissue being treated, particularly at the site of the tumor. Prior methods for measuring the temperature of the treated tissue employ thermocouples, thermometers or radiometers. One such method utilizing a radiometer is described in U.S. Pat. application, Ser. No. 808,272, filed on June 20, 1977 entitled "Apparatus for Hyperthermia Treatment" by Fred Sterzer.

Thermocouples for measuring the temperature of the treated tissue may be either attached to the surface of the skin or invasively positioned beneath the skin at or near the site of the tumor to be treated. Thermocouples are used while measuring temperature during treatment to switch off the microwave radiation to the tissue upon sensing a predetermined temperature. However, thermocouples positioned near or in close proximity to the irradiating signal distort the applied microwave signal inducing anomalous heating effects which contribute to inaccurate temperature control. It is known to measure the tissue temperature with a thermocouple only at a time when the irradiation signals are removed. Such an arrangement is described in the above-identified U.S. Pat. application, Ser. No. 840,036.

It is further known to utilize a thermometer disposed within a radio frequency radiating electrode to measure the temperature within the electrode, as described in U.S. Pat. No. 2,126,257, entitled "Electromedical Instrument," issued Aug. 9, 1938, to Frank E. Hird.

SUMMARY OF THE INVENTION

According to this invention, hyperthermia treatment of tissue is provided by irradiating tissue with microwave signals while simultaneously measuring the temperature of the irradiated tissues at the site of the applied microwave signals.

A coaxial applicator, having a shielded thermocouple, within the inner conductor, radiates the microwave signals to the treated tissue. The thermocouple is positioned at the site of the applied radiation continuously measuring the temperature of the treated tissue.

The voltage corresponding to the temperature of the treated tissue is compared to a voltage that corresponds to the temperature to control the application or interruption of the microwave signals.

DESCRIPTION OF THE PREFERRED EMBODIMENT

Figure 1:
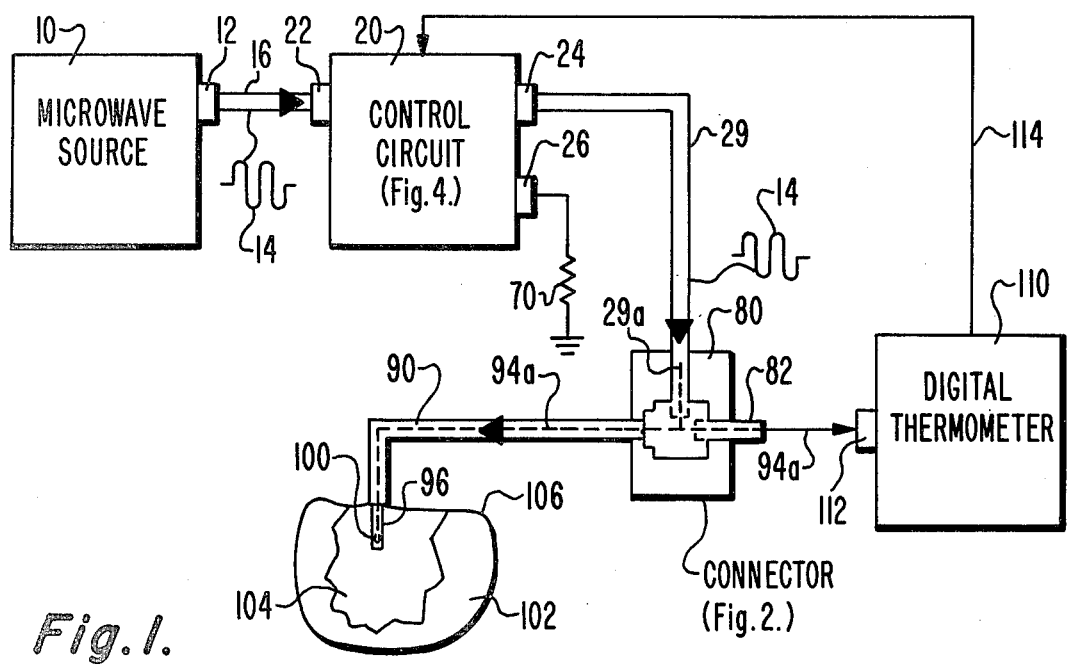
FIG. 1 is a block schematic of an apparatus utilizing the preferred embodiment of the invention.
Figure 2:
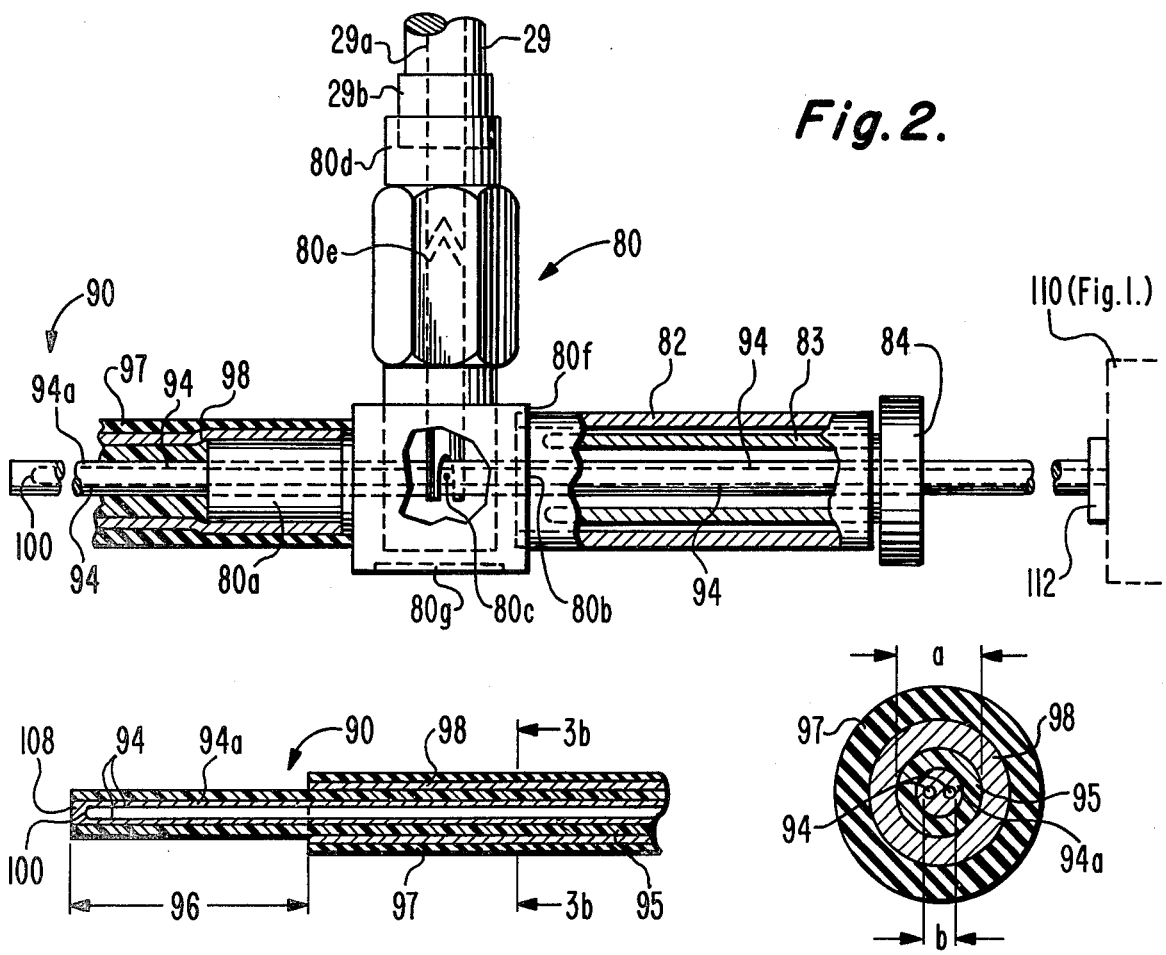
FIG. 2 is a detailed elevation view of the connector 80 of FIG. 1.

As shown in FIG. 1, microwave source 10 supplies a cw or pulsed microwave signal 14 for irradiation of tumor 104 during hyperthermia treatment. Signal 14 is coupled to control circuit 20 via coaxial connector 12, coaxial cable 16, and coaxial connector 22. Control circuit 20 couples the microwave signal 14 to tumor 104 via connector 24, coaxial cable 29 and coaxial right angle connector 80. The right angle connector 80 is a modified Model 1037-5002 connector manufactured by Omni-Spectra/Americon of Waltham, Mass. Coaxial cable 29 is attached to right angle connector 80 in a conventional manner whereby its center coaxial conductor 29a is extended into connector 80 (shown in detail in FIG. 2) and attached to hollow center conductor 94a of coaxial cable 20. Within the hollow conductor 94a of cable 90 (shown in detail in FIG. 3 to be described) are a pair of thermocouple wires 94 formed at one end into a thermocouple 100 and connected at the other end of the input connector 112 of a digital thermometer 110. Outer conductor 98 of coaxial cable 90 is separated from the central portion and slipped over a hollow nose portion 80a of connector 80, the center conductor 94a being extended into and through the connector 80 for connection to extension pin 80e as by soldering at 80c and thence to the center conductor 29a of coaxial cable 29. The soldering access hole 80g is suitably sealed after soldering the inner conductors. A male threaded coaxial coupler 29b attached to coax 29 couples center conductor 29a of coax 29 to connector 80 via a female rotatable threaded sleeve 80d. The thermocouple wire pair 94 and center conductor 94a are extended out through a suitable access hole 80b of connector 80 for connection to digital thermometer 110. A hollow telescopic brass slideable tuner slug 83 is fit within a hollow brass sleeve 82 attached to connector housing 80 in registration with a hole therein and over conductor 94a and the wire pair 94. Slug 83 is slideably adjusted within sleeve 82 as by knob 84 between the connector 80 and the digital thermometer 119 to reduce reflections produced by the thermocouple sleeve 94a extending out through the connector 80 and within the hollow sleeve 82 and other reflections generated at the right angle connector. Thus, the microwave energy from source 10 via cable 29 is efficiently coupled to cable 90 and thence the treated tumor tissue is decoupled from the thermocouple signal (to be described) conducted by the thermocouple wire pair 94.

As shown in FIG. 1, microwave signal 14 is radiated into tumor 104 via an unshielded end 96 of the coaxial cable applicator 90. Unshielded end 96 is positioned at the site of the tumor to be treated within tissue 102. The unshielded end 96 is invasively positioned within a subcutaneous tumor 104 beneath surface 106. The unshielded end 96 functions as a monopole antenna converting microwave signal 14 into irradiation fields within tumor 104. Located near the tip of the unshielded end 96 is thermocouple 100. Thermocouple 100 measures the temperature of tissue in contact with the end 96, in the known manner, the temperature of the tissue being manifested as a D.C. voltage developed by the thermocouple 100. This D.C. voltage is coupled to digital thermometer 110 via the thermocouple wire pair 94. Digital thermometer 110 is suitably a Model No. BAT-8 manufactured by the Bailey Instrument Co. of Saddle Brook, New Jersey. Digital thermometer 110 includes suitable circuits and logic to display digitally the temperature sensed by the thermocouple 100. Digital thermometer 100 provides a proportional D.C. voltage, suitably in a range of 0–3.0V, indicative of the thermocouple temperature, which is coupled to the control circuit 20 via signal path 114.

Figure 3A:
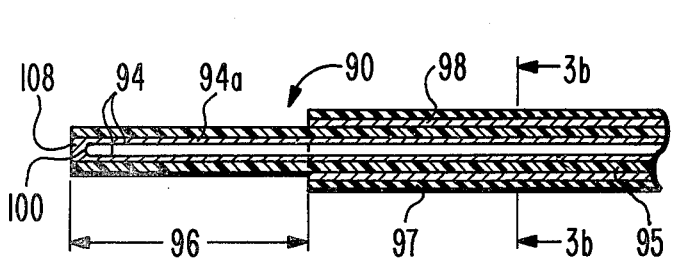
FIGS. 3a and 3b are sectional schematics of the coaxial cable applicator of the invention.
Figure 3B:
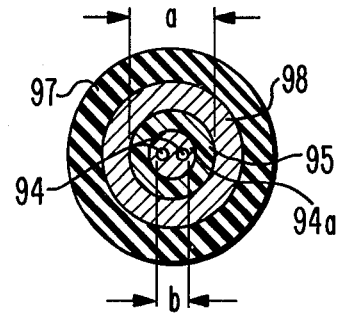

FIG. 3a illustrates in section a portion of the coaxial applicator 90, FIG. 3b being an end view thereof. Applicator 90 comprises a suitable vinyl jacket 97, outer conductor 98 formed of a suitable braided wire. The space between outer conductor 98 and center conductor 94a is filled with a suitable dielectric material 95 such as teflon. The thermocouple 100 is suitably an ungrounded, 304ss (stainless steel) sheathed, copper-constantan, Model Number SCPSS-02OU-6, manufactured by Omega Engineering, Inc. of Waltham, Mass. An end gap 108 is provided by the manufacturer to prevent the thermocouple 100 from being grounded to the inner conductor 94a. The center conductor 94a may be gold plated to improve its conductivity and reduce the eddy current effect in the thermocouple sleeve 94a produced by the microwave signal 14. The characteristics impedance (Zo) of coaxial applicator 90 can be represented by the formula:

$$Z_o = 138/\sqrt{\epsilon} \log_{10}(b/a) \quad (1)$$

where $\epsilon$ is the dielectric constant of the medium between the center (94a) and outer (98) conductor and a and b are respectively the center and outer conductor diameters. For a characteristic impedance of 50 ohnms, $1/\sqrt{\epsilon}$ is 0.69 for teflon, "a" equals 0.020 inches and "b" inches 0.067 inches.

The unshielded end 96 of center conductor 94a extends for a distance equal to $\lambda g/2$, or an integer multiple of $\lambda g/2$, $\lambda g$ being defined by the following relation:

$$\lambda g = C/f\sqrt{\epsilon} \quad (2)$$

where C is the speed of light in vacuum equal to 11.802874 inch-GHz, f is the microwave frequency in Gigahertz and $\epsilon$ is the dielectric constant of the area being irradiated.

In operation, microwave signal 14 is propagated in a radial direction about the unshielded end 96. In practice the braided wire 98 is completely removed or cut back from the circumference of unshielded end 96 allowing the microwave signal 14 to irradiate the tumor 104 located about unshielded end 96. Unshielded end 96 being essentially a probe functions as an omnidirectional antenna in the radial plane. Since the end 96 has an electrical length of $\lambda g/2$ or an integer multiple thereof, it functions to provide maximum radiation efficiency at frequency f.

Figure 4:
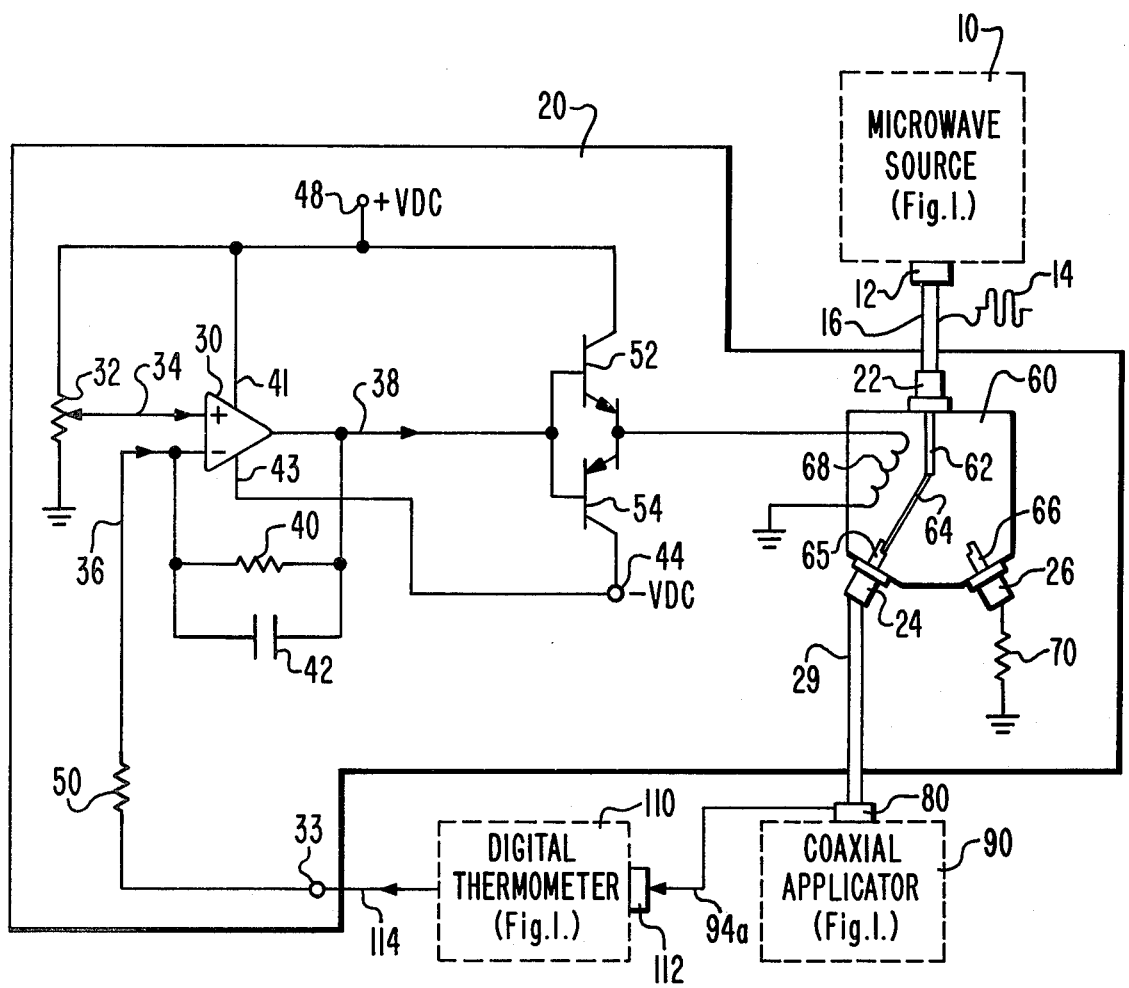
FIG. 4 is a schematic of a preferred controller circuit utilized in FIG. 1.

FIG. 4 is a schematic of control circuit 20, which interconnects the severed components of the system for the hyperthermia treatment. Coaxial switch 60 connects microwave signal 14 to either connector 80, for further transfer to tumor 104, or to the dummy load 70. Coaxial switch 60 is suitably a Hewlett-Packard switch part number 8761A. Switch 60 includes an input coaxial connector 22 and two output coaxial connectors 24 and 26, and a flexible reed contact 64 that is magnetically coupled to a winding 68. Each of the coaxial connectors 22, 24, and 26 have inner conductors 62, 65, and 66, respectively. Reed contact 64 is connected at one end to the center conductor 62 of the input connector 22, while the other end thereof is positionable in response to signals passing through the winding 68 to be electrically connected with either center conductor 65 or 66. The polarity of voltage applied to winding 68 determines the position to which reed contact 64 is connected. Thus, a positive voltage applied to winding 68 positions reed contact 64 to inner conductor 65 of the coaxial connector 24 and thus connects microwave signal 14 to applicator 90 via connector 80 for irradiation of tumor 104. A negative voltage applied to winding 68 positions reed contact 64 to inner conductor 66 and thus connects microwave signal 14 to dummy load 70. The application of a positive or negative energizing signal to winding 68 is controlled by a differential amplifier 30 operating with transistors 52 and 54. Differential amplifier 30 is suitably type RCA CA-741. Transistor 52 is a NPN type and transistor 54 is a PNP type.

Differential amplifier 30 has two inputs, one a non-inverting input on signal path 34 and the other an inverting input on signal path 36. The input on path 34 is preset to a D.C. value indicative of a predetermined temperature that is to be maintained during a hyperthermia treatment; e.g., 43° C. The preset value is set by adjusting potentiometer 32. The potentiometer 32 is connected between a voltage source having a particular polarity, such as a positive D.C. voltage, at terminal 48 and a reference voltage such as ground, such that the preset value is adjustable therebetween. The input voltage to amplifier 30 on path 36 is suitably a voltage within a range of 0 to 3 volts D.C. from digital thermometer 110 coupled to control circuit 20 via signal path 114, terminal 33, and resistor 50. The voltage is indicative of the temperature of the treated tumor 104 as measured by the thermocouple internal to center conductor 94a of coaxial applicator 90 at the site of the treatment. Differential amplifier 30 is connected to positive (48) and negative (44) supply voltages via paths 41 and 43, respectively.

Differential amplifier 30 produces an output voltage on path 38 proportional to a differential voltage existing between input paths 34 and 36. When the voltage signal on path 36 is less than the preset value at input 34, differential amplifier 30 produces a positive voltage on path 38 rendering transistor 52 conductive. Transistor 52 being conductive provides a positive voltage to winding 68 of coaxial switch 60 thereby providing the path for connecting microwave signal 14 to tumor 104. When the voltage signal on path 36 exceeds the preset value at input 34, a negative voltage is generated on path 38, turning off transistor 52 and allowing transistor 54 to be conductive. Transistor 54 being conductive provides a negative voltage to winding 68 of coaxial switch 60 thereby removing microwave signal 14 from tumor 104 and further connecting the microwave signal 14 to the dummy load 70. Resistor 40 and capacitor 42 connected between the inverting input path 36 and the output path 38 of amplifier 30 forms a feedback network that determines the gain of the differential amplifier in response to the differential signal between 34 and 36.

In operation, when the temperature of the treated tumor 104 as measured by the thermocouple 100 at the site of the treatment, is below the preset value as established by the potentiometer 32, the microwave signal 14 is coupled via switch 60 to irradiate tumor 104. The irradiation by signal 14 continues until the temperature of the treated tissue equals the preset value. This action is repeated as the switch 60 applies and disconnects signal 14 from the tumor 104 in response to the temperature of the tumor as sensed by the thermocouple 100.

Figure 5A:
FIGS. 5a and 5b are sectional schematics of a coaxial applicator modified to produce a directional radiator.
Figure 5B:
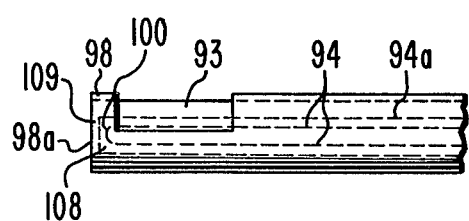

Another embodiment for radiating the microwave signal 14 to tissue, but in a selected direction is illustrated in FIGS. 5a and 5b. FIG. 5a is a plan view of the end portion of coaxial applicator 90 while FIG. 5b is a sideview thereof. The braided wire outer conductor 98 is cut out to provide a generally semicylindrical unshielded area 93 having a length in accordance with formula (2) given for unshielded end 96. The unshielded end portion 93 functions as a directional antenna for radiating microwave signal 14 in one general direction. The unshielded end 93 may be formed by removing only a portion of the braided wire at the end of applicator 90 as shown in FIGS. 5a and 5b. The braided wire 98 suitably covers the end of the coaxial applicator 90 as at 98a to prevent longitudinal propagation of microwave signal 14. Therefore, the center conductor 94a is shortened a distance to prevent it from touching the braided wire 98 as by gap 109. A gap 108 between the thermocouple and conductor 94a being similarly provided by the manufacturer as that for the applicator of FIG. 3a.

If desired a directive radiator can be fabricated by merely cutting back the shielded conductor 98 a sufficient distance to provide the desired radiator length for conductor 94a andd suitably forming a semi-cylindrical metallic reflector over the radiator portion to provide an unshielded portion similar to that shown in FIGS. 5a and 5b.

In practice the use of an unshielded end as an omnidirectional (FIGS. 3a and 3b) or directional antenna (FIGS. 5a and 5b) is dependent upon the form or location of the tumor to be treated. If it is desired to confine the microwave signal 14 to a particular direction for irradiation of a tumor, as existing in a surface portion, then partially shielded end 93 (FIGS. 5a and 5b) is used. If it is desired to radiate in a cylindrical volume, to treat a tumor 104, then unshielded end 96 (FIGS. 3a and 3b) is invasively positioned within the tissue.

It should now be appreciated that this invention provides an applicator for hyperthermia treatment for continuous irradiation of a microwave signal (14) into tissue (104) and concurrent measurement of the temperature at the site of the irradiated tissue (104). The temperature of the heat treated tissue is automatically controlled in response to the temperature being sensed by the thermocouple within the applicator. Since the thermocouple is isolated from microwave signals and yet thermally sensitive to the ambient tissue temperature, the invention overcomes the problem of thermocouples used in the prior art interfering with the irradiating microwave signals. Furthermore, since the thermocouple provided in the present applicator is in the radiator, it measures the temperature of the tissue continuously during the irradiation process. It should be further understood that the microwave signals used to practice the invention include electromagnetic signals in the radio frequency spectrum comprising, for example, 100 to 10,000 MHz.

What is claimed is:

1. Apparatus for hyperthermia treatment by irradiation of tissue with microwave energy comprising:
   a. source means for providing microwave signals;
   b. radiator means including a hollow radiating probe responsive to said microwave signals for irradiating said tissue with microwave energy;
   c. coaxial means for coupling said microwave signals to said radiator means,
      said coaxial means including a coaxial cable having a hollow center conductor and dielectic material between said center conductor and an outer cylindrical conductor, said coaxial center conductor being connected to said hollow radiating probe;
   d. thermocouple means including a thermocouple positioned within said hollow radiating probe and further including a pair of wires coupled to said thermocouple and extending through said hollow probe and said hollow conductor of said coaxial cable for providing electrical signals indicative of the temperature of said irradiated tissue; and
   e. control means responsive to said electrical signals for coupling said microwave signals to said radiator means when the temperature of said irradiated tissue is less than a predetermined temperature.

2. Apparatus according to claim 1, wherein said probe has a length equal to an integer multiple of one half the wavelength of the frequency of the microwave signals.

3. Apparatus according to claim 2, wherein said probe is shielded to provide a directional radiator of the microwave energy.

4. Apparatus according to claim 1, further including thermometer means responsive to said electrical signals for generating a tissue temperature signal indicative of said tissue temperature, and wherein said coaxial means includes a right angle coaxial connector, a first coaxial cable connecting said source means to said connector, and a second coaxial cable connecting said connector to said probe, said second cable including said thermocouple means, said connector including means for extending said pair of thermocouple wires from said second cable to said thermometer means.

5. Apparatus according to claim 4, further including hollow cylindrical tuning means coupled to said connector and surrounding said pair of wires for reducing microwave signal reflections generated at said connector.

6. Apparatus according to claim 4, wherein said control means comprises:
   a. means for generating a first electrical signal indicative of a predetermined reference temperature;

b. means responsive to said first electrical signal and said tissue temperature signal for producing an output control signal when said first electrical signals exceeds said tissue temperature signal;
c. means responsive to said output control signal to couple said microwave signals to said radiator means; and
d. means responsive to the absence of said output signal to decouple said microwave signals from said radiator means.

7. Apparatus for hyperthermia treatment by irritation of tissue with microwave energy and monitoring of tissue temperature at a remote monitoring means comprising:
a coaxial cable having a hollow first conductor and a second conductor larger than and coaxial with said first conductor to form a transmission line cable, a portion of said hollow first conductor extending beyond said second conductor to form a radiator of microwave signals conducted by said coaxial cable,
a temperature sensing means within said extended portion for providing temperature signals indicative of the ambient temperature about said extended portion and means extending through said hollow first conductor for coupling said temperature signals from said temperature sensing means to said monitoring means for remotely providing an indication of the temperature of the tissue heated by microwave signals at said radiator.

8. The combination of claim 7 wherein said temperature sensing means is a thermocouple and said means for coupling is a pair of wires.

9. The combination of claim 7 including control means responsive to said temperature signals for coupling said microwave signals to said radiator means when the temperature of said irradiated tissue is less than a predetermined temperature.

* * * * *